(12) United States Patent
Voien

(10) Patent No.: US 8,771,185 B2
(45) Date of Patent: Jul. 8, 2014

(54) SYSTEM AND METHOD FOR RELIABLE SLEEP DIAGNOSTIC TESTING

(75) Inventor: Dana Voien, Laguna Niguel, CA (US)

(73) Assignee: Sleepsafe Drivers, Inc., Laguna Niguel, CA (US)

( * ) Notice: Subject to any disclaimer, the term of this patent is extended or adjusted under 35 U.S.C. 154(b) by 407 days.

(21) Appl. No.: 12/928,903

(22) Filed: Dec. 22, 2010

(65) Prior Publication Data

US 2012/0165628 A1   Jun. 28, 2012

(51) Int. Cl.
*A61B 5/00* (2006.01)
*G06F 19/00* (2011.01)
*G09F 3/03* (2006.01)
*A61B 5/02* (2006.01)

(52) U.S. Cl.
CPC .............. *G06F 19/3418* (2013.01); *G09F 3/03* (2013.01); *A61B 5/02* (2013.01)
USPC ........... 600/300; 600/301; 600/323; 600/324; 383/5

(58) Field of Classification Search
USPC ........................ 600/300, 301, 323, 324; 383/5
See application file for complete search history.

(56) References Cited

U.S. PATENT DOCUMENTS

| | | | | |
|---|---|---|---|---|
| 5,452,930 | A * | 9/1995 | Morgan ..................... | 292/307 A |
| 6,588,812 | B1 * | 7/2003 | Garcia et al. .............. | 292/307 R |
| 6,915,802 | B1 * | 7/2005 | Anderson et al. ........ | 128/203.15 |
| 7,423,526 | B2 * | 9/2008 | Despotis .................. | 340/539.12 |
| 7,849,619 | B2 * | 12/2010 | Mosher et al. ................. | 40/633 |
| 8,308,640 | B2 * | 11/2012 | Baldus et al. ................ | 600/300 |
| 8,410,926 | B1 * | 4/2013 | Gary et al. ............... | 340/539.12 |
| 8,474,584 | B2 * | 7/2013 | Mrocki et al. ................ | 190/101 |
| 2002/0115919 | A1 | 8/2002 | Al-Ali | |
| 2004/0025866 | A1 * | 2/2004 | Vedrine et al. ........... | 128/200.19 |
| 2004/0084047 | A1 * | 5/2004 | Hickle ...................... | 128/203.13 |
| 2004/0138535 | A1 * | 7/2004 | Ogilvie ......................... | 600/300 |
| 2004/0260154 | A1 | 12/2004 | Sidelnik et al. | |
| 2005/0125363 | A1 * | 6/2005 | Wilson et al. .................... | 705/75 |
| 2006/0225332 | A1 * | 10/2006 | Zenisek .......................... | 40/638 |
| 2007/0015728 | A1 * | 1/2007 | Ford ................................ | 514/49 |
| 2007/0017136 | A1 * | 1/2007 | Mosher et al. .................. | 40/633 |
| 2007/0073116 | A1 | 3/2007 | Kiani et al. | |
| 2007/0199567 | A1 * | 8/2007 | Kanzer ...................... | 128/206.21 |
| 2008/0041379 | A1 * | 2/2008 | Turiello .................... | 128/204.21 |
| 2008/0076995 | A1 * | 3/2008 | Hoarau ......................... | 600/344 |

(Continued)

FOREIGN PATENT DOCUMENTS

WO   PCT/US2011/065646   12/2011

OTHER PUBLICATIONS

U.S. Appl. No. 13/328,995, filed Dec. 16, 2011.

(Continued)

*Primary Examiner* — Gary Jackson
*Assistant Examiner* — Bobby Soriano
(74) *Attorney, Agent, or Firm* — Mintz Levin Cohn Ferris Glovsky and Popeo, P.C.

(57) ABSTRACT

A method for securely affixing a sensor to a patient is provided. The method includes attaching the sensor to the patient's index finger with a sensor signal cable routed along the patient's hand, and configuring an identification band to encircle the signal cable and the patient's wrist using a secure affixing arrangement. The identification band is configured to evidence tampering when removed. The secure affixing arrangement may take various forms, including tying loops and securing the cable and/or sensor to the patient using tape, plastics, and so forth.

18 Claims, 21 Drawing Sheets

(56) References Cited

U.S. PATENT DOCUMENTS

| | | | |
|---|---|---|---|
| 2008/0221402 A1* | 9/2008 | Despotis | 600/301 |
| 2008/0257673 A1* | 10/2008 | Mrocki et al. | 190/101 |
| 2009/0212957 A1* | 8/2009 | Burris | 340/573.4 |
| 2010/0056886 A1 | 3/2010 | Hurtubise et al. | |
| 2010/0312075 A1* | 12/2010 | McGonigle et al. | 600/301 |
| 2011/0115221 A1* | 5/2011 | Kaplan | 289/1.2 |
| 2011/0213255 A1* | 9/2011 | Finburgh et al. | 600/490 |
| 2012/0108983 A1* | 5/2012 | Banet et al. | 600/480 |
| 2012/0190949 A1* | 7/2012 | McCombie et al. | 600/324 |

OTHER PUBLICATIONS

Powell et al., "The Road to Danger—The Comparative Risks of Driving While Sleepy" Laryngoscope 111: May 2001.

DOT/FMCSA, Medical Review Board's Recommendations of Jan. 2008.

Hartenbaum, Natalie, "The DOT Medical Examination: A Guide to Commercial Drivers' Medical Certification" Nov. 8, 2011.

Peaco, Ed, "Truckers scrutinized for sleep apnea," Nov. 14, 2011.

Nunlist, Tom and Oliver B. Patton, "A better Way to Drug Test? Hair Testing Reveals Disturbing Facts About Driver Drug Use and DOT Requirements," Nov. 21, 2011.

Hartenbaum, Natalie, "Transportation and Obstructive Sleep Anea Health, Saftey & Productivity Risks" Nov. 11, 2011.

Transcription of US National Transportation Safety Board hearing, in the matter of: "Public Forum on Truck and Bus safety: A Decade of Progress," May 11, 2011.

WikiHow Article, "How to Pass a Drug Test". Retrieved from the internet on Mar. 13, 2012.

Sharwood, Lisa N. et al., "Assessing Sleepiness and Sleep Disorders in Australian Long-Distance Commercial Vehicle Drivers: Self-Report Versus an "At Home" Monitoring Device," Sleep, vol. 35, No. 4, pp. 469-475, 2012.

PCT International Search Report and Written Opinion dated Jun. 21, 2012 for PCT application No. PCT/US2011/065646.

* cited by examiner

SYSTEM AND METHOD FOR RELIABLE SLEEP DIAGNOSTIC TESTING

BACKGROUND OF THE INVENTION

1. Field of the Invention

The present invention relates generally to sleep study monitoring and recording, and more specifically to securing a sensor, such as an oxygen saturation sensor, to an individual for purposes of conducting a sleep study.

2. Description of the Related Art

Sleep apnea is a disorder affecting many individuals, and the disorder can have various adverse consequences, including death in the most extreme circumstances. One area where sleep apnea is of particular concern is when persons are performing "risk sensitive" job activities, such as operating dangerous machinery, including driving vehicles on public roads.

A driver impairment study directed by Doctor's Nelson Powell and Robert Riley was conducted at the General Motors proving grounds. The study results were published in Laryngoscope 111: May 2001, in a paper titled—'The Road to Danger—The Comparative Risks of Driving While Sleepy'.

In summary, the Powell and Riley study revealed that eleven measured reaction time metrics for various individuals showed that sleepy drivers were the same as the alcohol-challenged drivers when operating a car and attempting to avoid obstacles. These results are widely accepted as suggesting that driving while sleepy should be recognized as potentially dangerous or as at least as dangerous as driving while under the influence of alcohol.

In view of dangers of driving while sleepy and an understanding of the effects of obstructive sleep apnea, the Department of Transportation continues to modify requirements for a commercial vehicle driver to be deemed "Fit for Duty." The DOT/FMCSA released their Medical Review Board's Recommendations of January 2008, where the Sleep Apnea Guidelines include monitoring drivers for symptoms and potential diagnosis for sleep apnea.

Sleep apnea testing, screening, and monitoring requirements have created an environment where individuals wishing to obtain or keep a commercial drivers license are fearful of failing the sleep apnea test, and thus having their license refused or revoked. The fear of losing a job has led some drivers to introduce fraud during ambulatory sleep apnea monitoring. For example, the individual being monitored may switch their oxygen saturation-monitoring device to another person who may be known to present an acceptable oxygen saturation level. The person believed to have acceptable levels wears the device during his sleep period, thereby providing a false negative indication for apnea in the desired test subject.

Current methods and designs may become problematic during ambulatory studies when the test individual is not under direct supervision. Ambulatory, i.e. portable, sleep apnea tests can be hours in duration and are typically set up in a sleep lab, test subject's home, truck cab, or a hotel. Signals are recorded while the patient is asleep. Prior to or during the testing stage of the oxygen saturation monitoring procedure, the patient being studied may remove the sensing device and give the device to another individual believed to have satisfactory saturation levels. Also, current designs may fail to properly exhibit evidence of tampering when an individual attempts to remove the testing device and associated apparatuses.

With in-patient polysomnography sleep lab supervised tests, fraud may occur by simply having another individual take the desired individual's test by presenting a fake identification such as a non-commercial driving license. Many of today's labs currently operate without checking the patient's identification and presume the person present is the person referred for the test.

Based on the foregoing, it would be beneficial to offer a method for safely and securely conducting an ambulatory sleep apnea test, where the sensing device is secured to the test individual in a tamper resistant or tamper evident manner.

SUMMARY OF THE INVENTION

According to one aspect of the present design, a method for reliable sleep testing, or oxygen saturation monitoring, is provided. The method includes attaching the sensor to the patient's index finger with a sensor signal cable routed along the patient's hand, and configuring an identification band to encircle the signal cable and the patient's wrist using a secure affixing arrangement. The identification band is configured to evidence tampering when removed. The secure affixing arrangement may take various forms, including tying loops and securing the cable and/or sensor to the patient using tape, plastics, and so forth.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which.

DETAILED DESCRIPTION OF THE INVENTION

Figure 1:
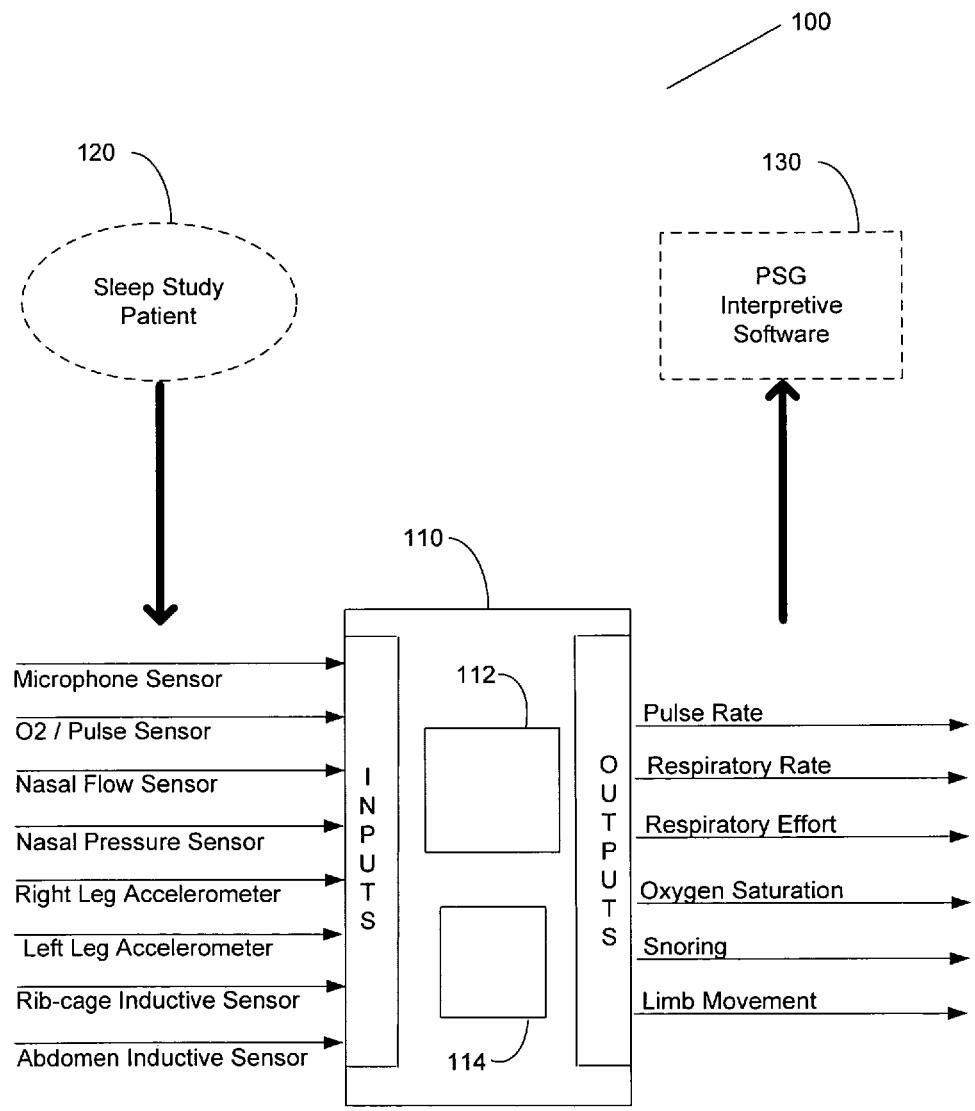
FIG. 1 represents an exemplary portable sleep diagnostic testing and monitoring system in a functional block diagram to show the major components and interfaces for a monitoring and recording instrument that may be employed in accordance with an aspect of the present design.

The following description and the drawings illustrate specific embodiments sufficient to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design is directed to securing a pulse oximetry sensing device (e.g. oxygen saturation sensor), and associated signal cable, using a device such as an identification band, with a tearable and/or shredable region, for attaching the sensor to the test subject (e.g. patient) during ambulatory sleep monitoring and recording.

The identification band arrangement may fix the sensing device and signal cable to the patient in a manner sufficient to reliably monitor the test subject, by protecting the sensor device from tampering and decreasing the likelihood of potential test fraud during sleep apnea testing. Such operation may occur when a respiratory therapist (e.g. clinician) follows the installation protocol called for herein.

The system disclosed may include, but is not limited to, at least one identification band device in combination with a finger sensor device configured with a signal cable for affixing and positioning the sensor and cable prior to undergoing testing.

The installation protocol further includes providing for accurate test subject identification and education prior to starting the procedure. The present design may involve, but is not limited to, inter looping of two identification bands, requiring patient's to mark his or her identification band, inter looping the signal cable to circle around the identification band, and for applying a shearable tape, such as packing tape, to partially cover the sensor and cable.

The present design may enable the respiratory therapist to identify evidence, for example a torn identification band or a sheared tape, resulting from an attempt to manipulate the monitored results.

While generally described herein as a reliable, more tamper resistant and secure method for affixing a pulse-oximetry sensor for ambulatory PSG monitoring, the present design may be used with other testing devices employing a sensor affixed to the patient. Ambulatory sleep diagnostic testing and monitoring may further involve the use of other types of sensors such as accelerometers (measuring limb movement), and inductive bands (monitoring breathing characteristics, such as effort and rate). The methods and protocols disclosed herein may be used for securing these additional sensor types in a generally tamper-proof manner. For example, an accelerometer may be attached to each of the patient's legs, and/or inductive bands may be attached to the patient's chest, secured in accordance with the present design.

The present design may be applied to other forms of ambulatory sensor based monitoring, including for example to document sleep behaviors and patterns, circadian rhythm, respiration measurements, hyper and hypo-activity, and cardiac output that may be associated with study procedures such as found in electrocardiography and electroencephalography.

The present design is not limited to ambulatory testing. For example hospital facilities, in-patient labs, and the military may use the present reliable monitoring system for overnight or "at home" testing. The present design can provide for a safe, comfortable, reliable, and tamper resistant sensor deployment in conjunction with a portable PSG monitoring and recording system.

System Example

While the present design may be used in various environments and applications, it will be discussed herein with a particular emphasis on an ambulatory sleep study environment where a respiratory therapist or health care practitioner affixes sensing devices to a patient/test subject prior to conducting a test. For example, one embodiment of the present design is in conjunction with a sleep diagnostic testing, monitoring and recording medical system that comprises an independent recorder module and pulse-oximetry sensor device connected by a signal cable.

FIG. 1 illustrates a functional block diagram of a portable sleep diagnostic test medical system 100 including the major components and interfaces for a monitoring and recording instrument that may be employed in accordance with the present design. Portable sleep diagnostic test recorder 110 may receive multiple communication signals delivered from individual cables attached to sensors positioned on sleep study patient 120. The signals may be received from a microphone sensor, an oxygen saturation/pulse sensor, nasal flow and pressure sensors, right and left leg accelerometers, and/or inductive sensors placed at the abdomen and at the rib cage.

Portable sleep diagnostic test recorder 110 may include processor 112 and memory 114 to monitor and record the received input sensor signals. Sleep diagnostic test recorder 110 may process the received communication signals and convert the signals into data and information readable by interpretive software 130.

Interpretive software 130 may receive the communication signals from the sleep diagnostic test recorder and present the information on a display monitor device, not shown, for review by the respiratory therapist, doctor, or other appropriate individual. The interpretive software may receive information from sleep diagnostic test recorder 110 and present graphical representations and/or cumulative results for monitored patient's pulse rate, respiratory rate and effort, oxygen saturation, snoring, and limb, i.e. leg, movement, and so forth.

Figure 2:
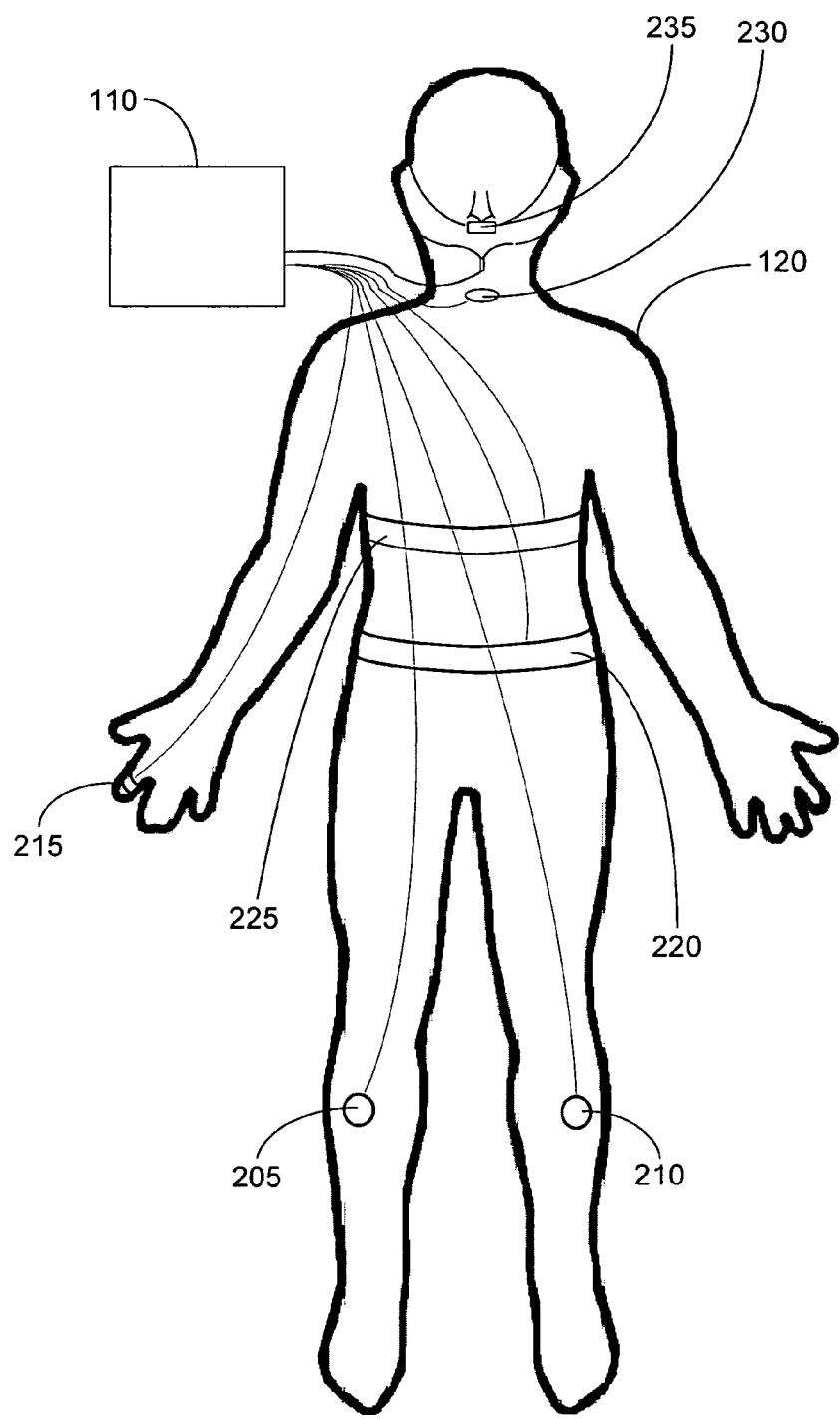
FIG. 2 shows a portable sleep diagnostic testing and monitoring system configured to receive signals from an array of sensors affixed to a patient for sleep apnea monitoring.

FIG. 2 illustrates a portable sleep diagnostic test polysomnography medical system 200 configured to receive signals from an array of sensors affixed to a patient in order to monitor sleep apnea characteristics. This configuration includes right leg accelerometer 205 and left leg accelerometer 210, pulse-oximetry sensor, abdomen inductive sensor 220, rib-cage inductive sensor 225, microphone 230, and nasal flow sensor/pressure sensor 235.

Reliable Sensor Monitoring

The present design provides a method or protocol for providing reliable oxygen saturation monitoring for ambulatory sleep apnea monitoring. The protocol may provide for relatively secure, tamper evident, uninterrupted measuring, and an efficient and effective means for managing ambulatory testing. The protocol may provide education and specific instructions to the patient prior to test conduct.

The present design may involve a Type 1 Monitoring device configured for use during in-lab polysomnography monitoring, or may involve a Type 2, 3, or 4 Monitoring device configured for use during ambulatory polysomnography monitoring.

Before commencing with testing, the present design may involve educating the patient by explaining the reasons behind the protocol and procedures about to be used. Education may include, but is not limited to, discussing the need for reliable results, addressing situations where previous patients have invalidated their results, such as switching the sensor device with another individual, obtaining a baseline measurement for comparison and validation of test outcome, in the context of preventive measures that ensure the accuracy of the test results.

Figure 3A:
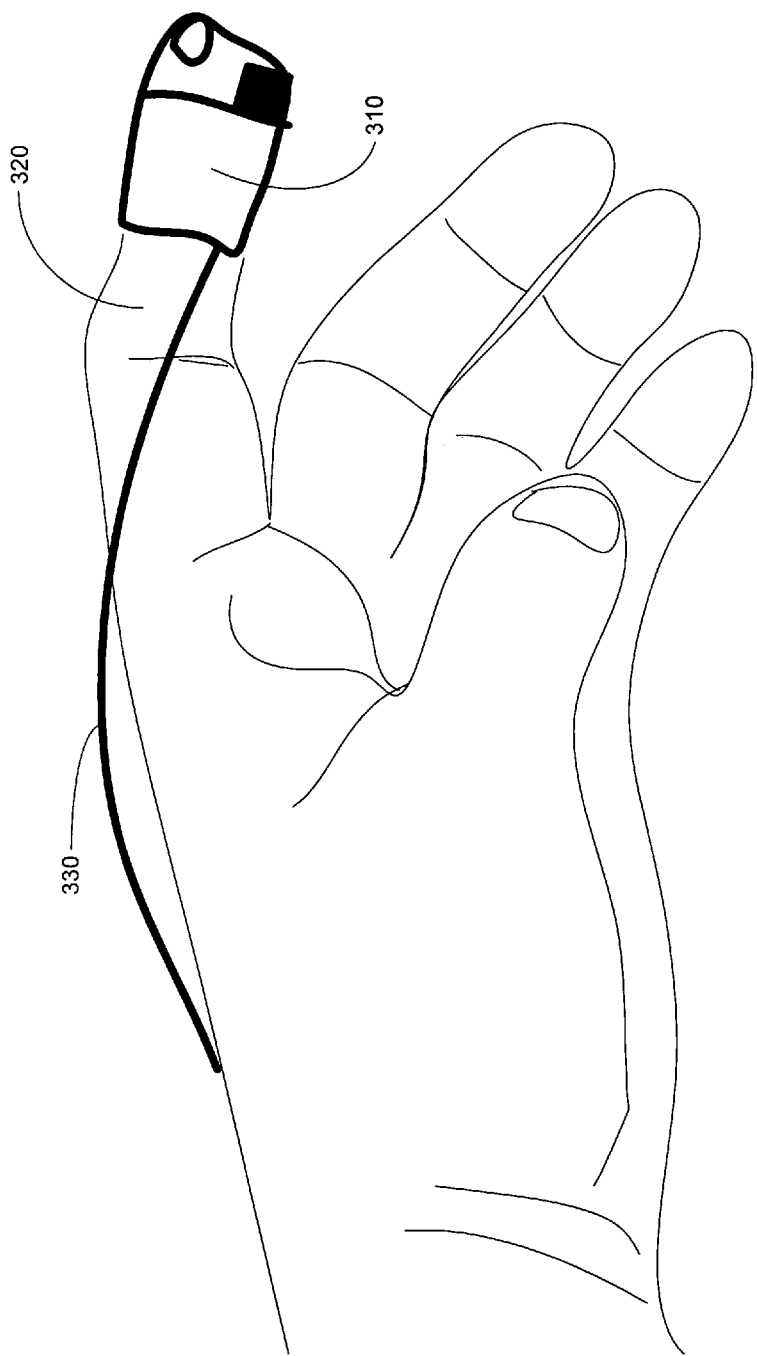
FIG. 3A illustrates a generalized view of an exemplary oxygen saturation sensing device design for use in sleep study monitoring.

FIG. 3A illustrates a generalized view of an exemplary oxygen saturation sensing device design for use in sleep study monitoring. The present design may be configured to work with currently approved Type II, Type III, and Type IV pulse-oximetry oxygen sensing devices.

A respiratory therapist, doctor, registered polysomnographic technologist, clinician, or other operator may position oxygen sensor 310 over patient's index finger 320 and attach the sensor, typically employing an adhesive backing mechanism, in accordance with directions for employing the sensor. Oxygen sensor 310, such as a pulse-oximetry sensor, may communicate signals to a PSG recorder over signal cable 330. Signal cable 330 may be routed along the hand, backside of wrist, and along the arm of the patient in a comfortable manner, such as using the patient's non-dominant arm. The respiratory therapist may check the patient's commercial or regular driver's license, passport, and like documentation to positively confirm patient's identity, and record the identifying information on a test form. In addition, the therapist may record serial numbers from one or more identification bands and the date and time of study. The therapist may ask the patient to review the test form for accuracy and then sign the form.

Figure 3B:
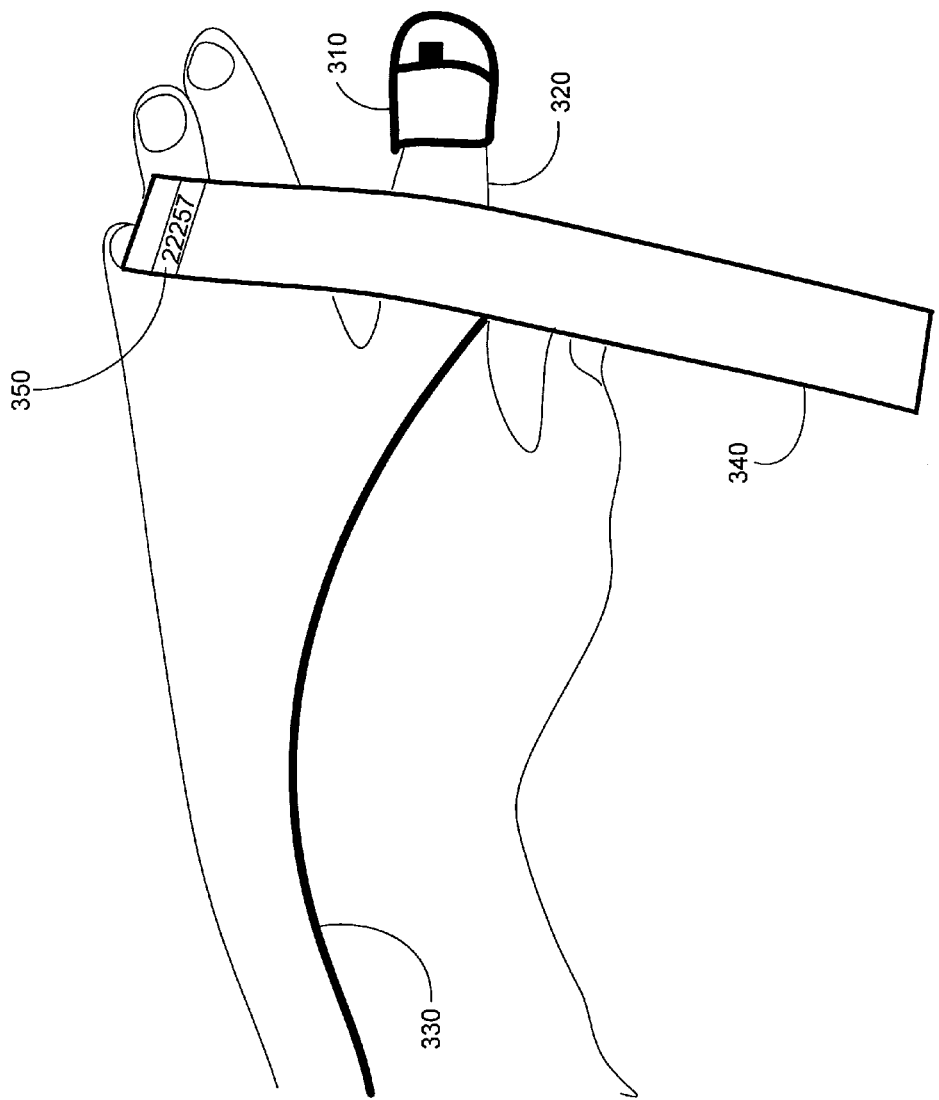
FIG. 3B is an exemplary identification band positioned to cover a oxygen saturation sensing device signal cable and lay across a patient's index finger.

FIG. 3B illustrates an exemplary identification band positioned to cover an oxygen saturation sensing device signal cable and lay across a patient's index finger. The identification bands may include tamper-proof bands. In one embodiment, the present design may involve identification bands exhibiting unique serial numbers, markable such as by using a pen, and the band's material shreds and/or tears when removed. Suitable materials for constructing the disclosed identification bands may include, but is not limited to, Tyvek®, plastic, vinyl, polyvinyl chloride (PVC), and various metals and fabrics. The present design may configure one of these materials, or a combination of these materials, for exhibiting tampering evidence when removed, such as tear marks resulting from being torn and shredded during removal.

Identification band 340 is positioned over the patient's index finger 320 where oxygen sensor 310 is attached. The respiratory therapist may lay identification band 340 in a near perpendicular relationship to the patient's index finger and arranged to cover signal cable 330. FIG. 3B illustrates the identification bands integral serial number 350 facing outward in a manner for easy viewing.

Figure 3C:
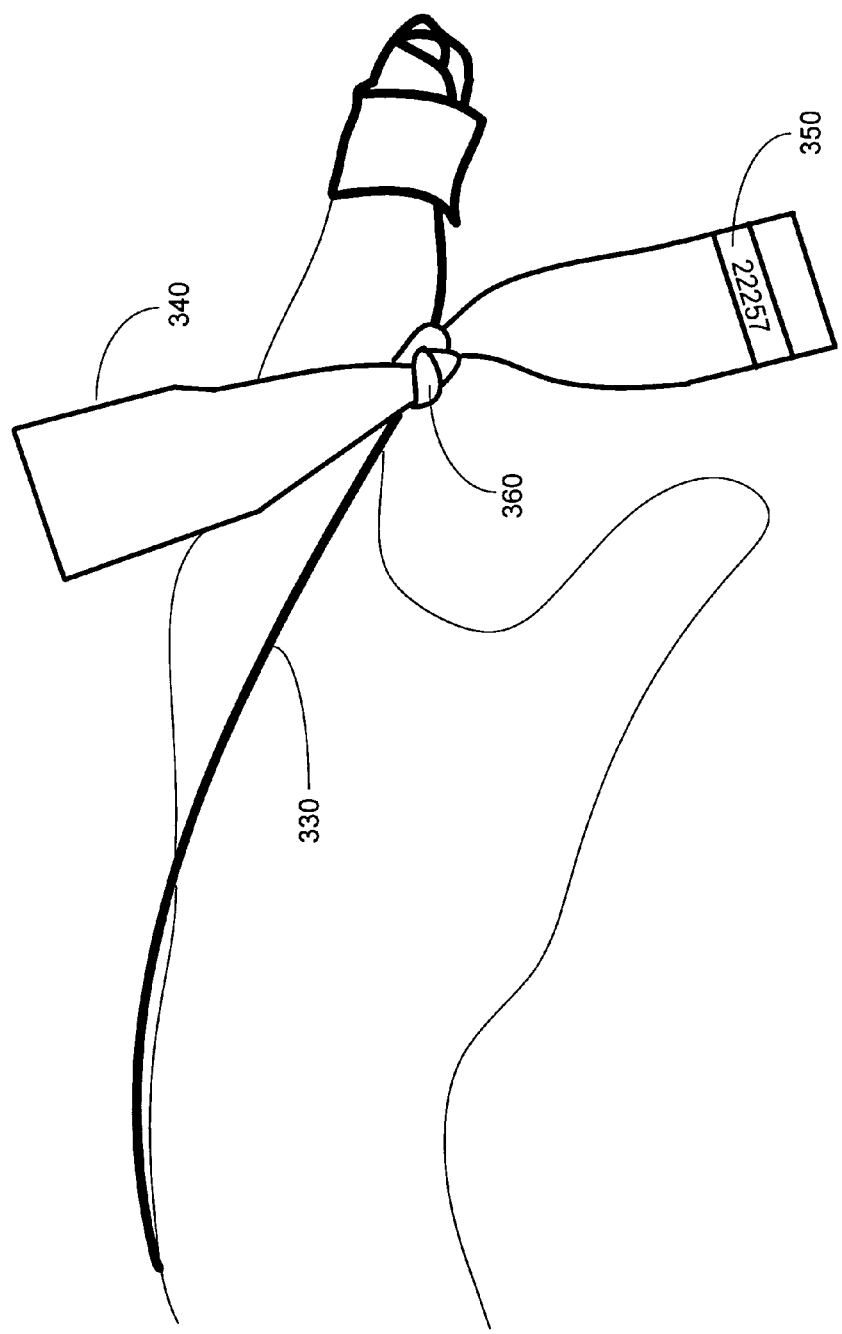
FIG. 3C represents an identification band tied in a knot around the oxygen saturation sensing device signal cable positioned at a patient's index finger.

FIG. 3C illustrates an identification band tied in a knot around the oxygen saturation sensing device signal cable positioned at the patient's index finger. The respiratory therapist may configure identification band 340 by forming a loop arrangement available for routing signal cable 330 through the loop and then tighten the loop creating knot 360 in the identification band encircling around the signal cable. Knot 360 may include, but is not limited to, types such as overhand, clove hitch, sheet, bowline, and figure eight. Independent of the knot type employed, proper tying and securing are paramount to successful deployment.

Figure 3D:
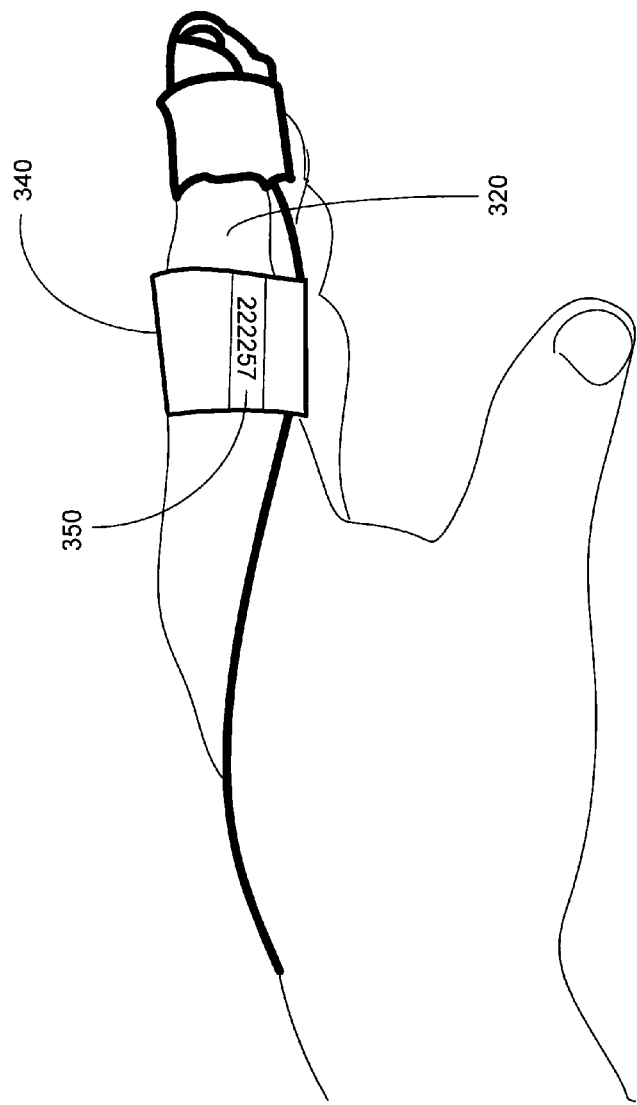
FIG. 3D is an identification band affixed to itself and in an arrangement to position the identification number for viewing by a register therapist.

FIG. 3D illustrates identification band 340 affixed to itself and in an arrangement to position serial number 350 for viewing by appropriate personnel, such as a respiratory therapist. After the knot is tightened around the signal cable, sufficient for securing the band to the cable, the respiratory therapist may wrap each end of identification band 340, in opposite directions, to encircle patient's index finger 320. In the case of an adhesive based band, the therapist may remove the protective backing and affix the band ends together. Other band types may be affixed to the patient according to the band manufacturer instructions. For example a band that employs a single snap on one end of the band, and provides a mate to the snap at the opposite end of the band, may entail the therapist aligning the snap with the mate to affix the band.

The present design may provide a secure, proof-positive, and uninterruptable sensor device-to-patient arrangement, sufficient for realizing reliable oxygen saturation measurements.

Figure 3E:
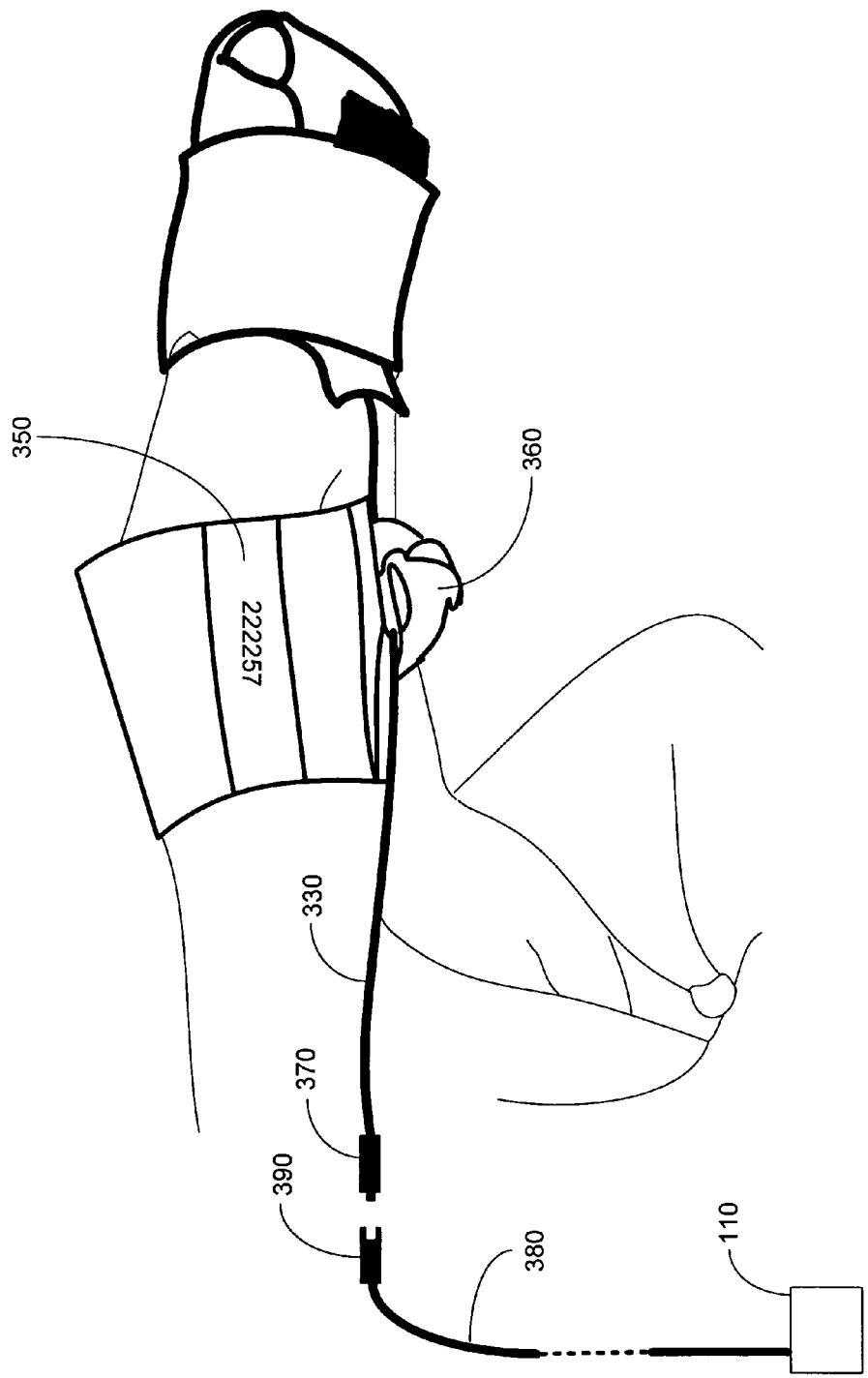
FIG. 3E shows a close up perspective view of the signal cable passing through a knot formed by the identification band.

FIG. 3E is a close up perspective view of signal cable 330 passing through knot 360 formed by affixing the band ends together in accordance with the method disclosed herein. Signal cable 330 may provide connector 370 for attaching signal cable 380 at connector 390 to communicate sensor signals for monitoring and recording by portable PSG recorder 110. Prior to test conduct, connector 370 is joined with connector 380 to complete the signal path. Serial number 350 is shown positioned for easy viewing by a register therapist. In another embodiment, the therapist may add a separate identification band by where the band is looped around the connection of signal cable 330 and the PSG recorder signal cable 380 where the cables meet and connect via connector 370 being plugged into connector 390.

The present design may involve the therapist recording a baseline pulse measurement as a further identity check prior to ambulatory test conduct. The baseline pulse measurement may be use as a profile for checking the test results. The check may include matching the patient's test results with the previously recorded baseline measurement. In the situation where the profile does not match the test results, the test outcome is deemed unreliable.

Figure 4A:
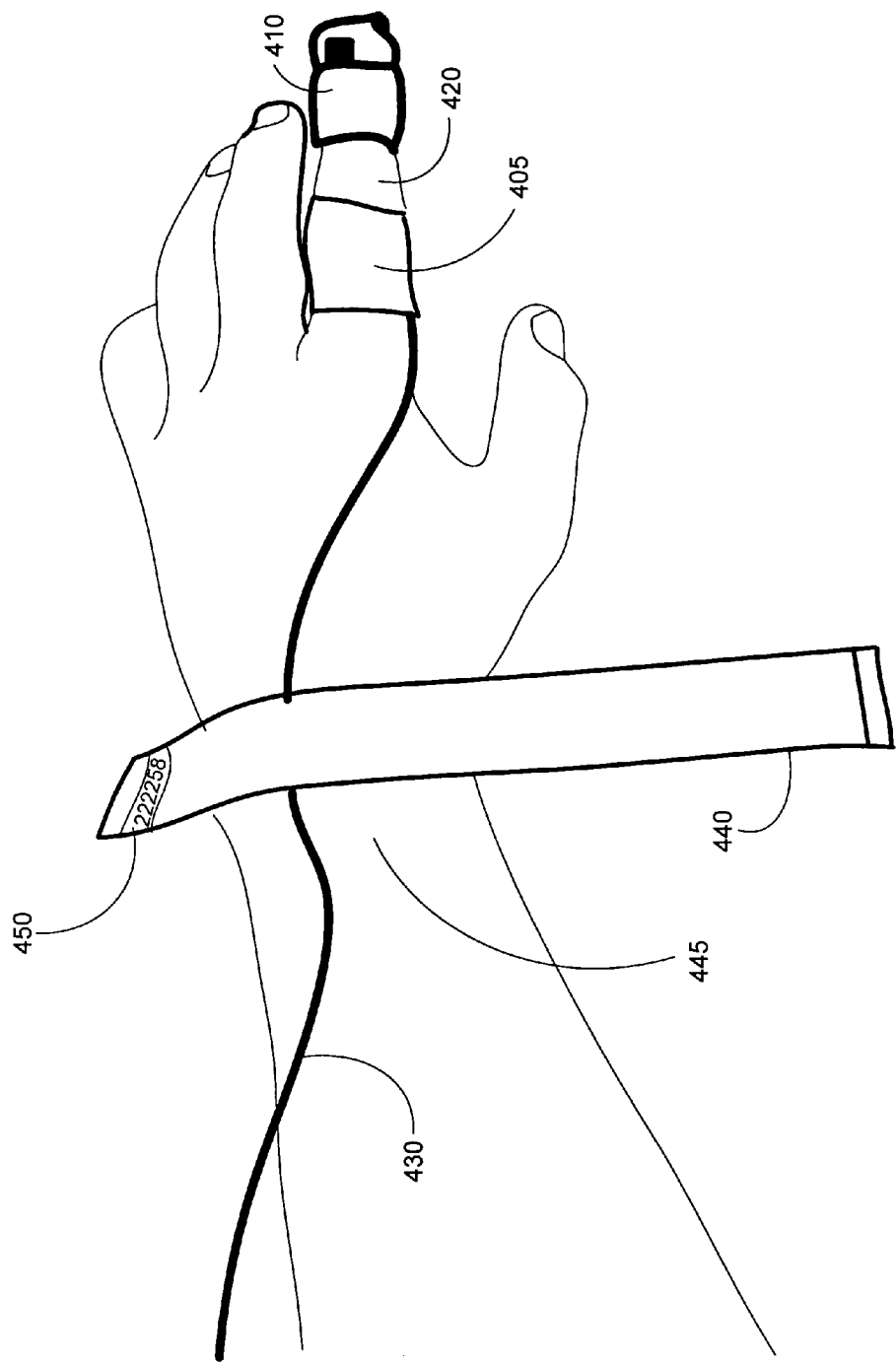
FIG. 4A illustrates an exemplary identification band positioned to cover the oxygen saturation sensing device signal cable and lay across a patient's wrist.

FIG. 4A illustrates an exemplary identification band positioned to cover the oxygen saturation sensing device signal cable and lay across a patient's wrist. The identification bands may be tamper-proof, numbered using a unique serial number, and/or designed to shred and/or tear when removed band types previously described and shown in FIGS. 3B-3E. Identification band 405 and pulse-oximetry sensor device 410 are shown attached to index finger 420.

Identification band 440 is positioned over the patient's wrist 445 and signal cable 430 originating from sensor device 410. The respiratory therapist may lay identification band 440 in a near perpendicular relationship to the patient's wrist and arranged to simultaneously cover signal cable 430. FIG. 4A illustrates the identification band's integral serial number 450 facing outwards in a manner for easy viewing.

Figure 4B:
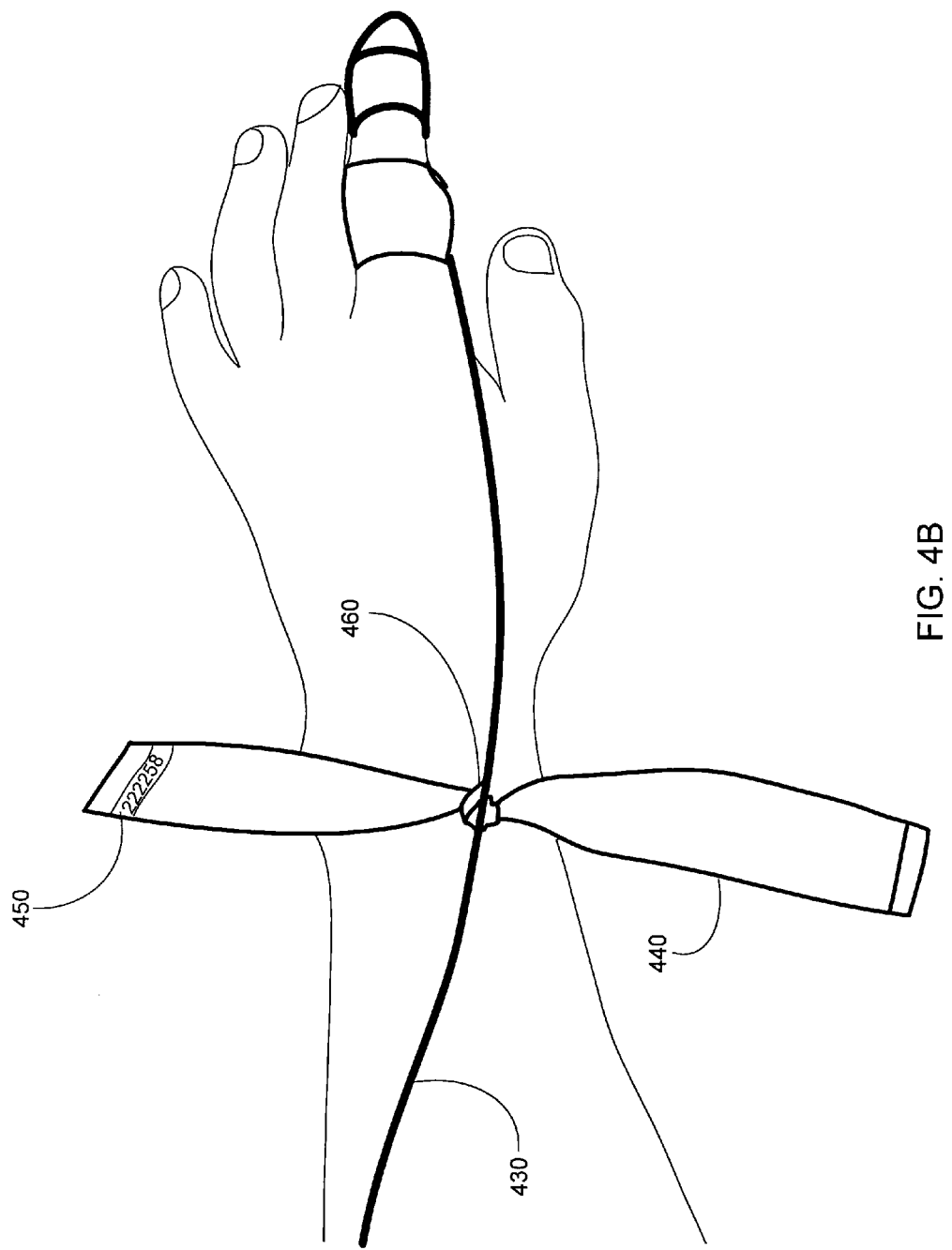
FIG. 4B represents an identification band tied in a knot around the oxygen saturation sensing device signal cable positioned at the patient's wrist.

FIG. 4B illustrates an identification band tied in a knot around the oxygen saturation sensing device signal cable positioned at the patient's wrist. The respiratory therapist may configure identification band 440 by forming a loop arrangement available for routing signal cable 430 through the loop and then tighten the loop creating knot 460 in the identification band encircling around the signal cable. The therapist may ensure knot 460 is properly tied and secured prior to placing in-use.

Figure 4C:
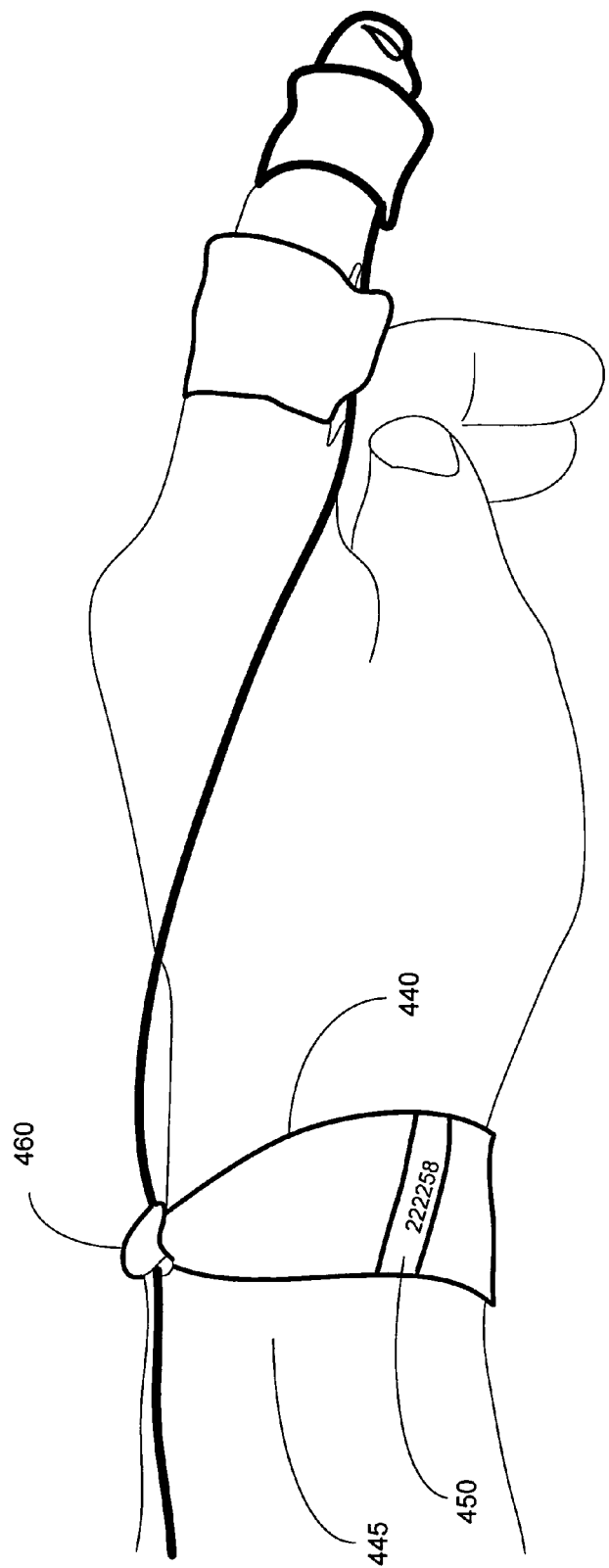
FIG. 4C shows an identification band affixed to itself and arranged to position the serial number for viewing by a respiratory therapist.

FIG. 4C illustrates identification band 440 affixed to itself and arranged to position serial number 450 for viewing by a respiratory therapist. After the knot is tightened around the signal cable, sufficient for securing the band to the cable, the respiratory therapist may wrap each end of identification band 440, in opposite directions, to encircle patient's wrist 445. Band types may be affixed to the patient's wrist in according to manufacturer instructions.

Figure 4D:
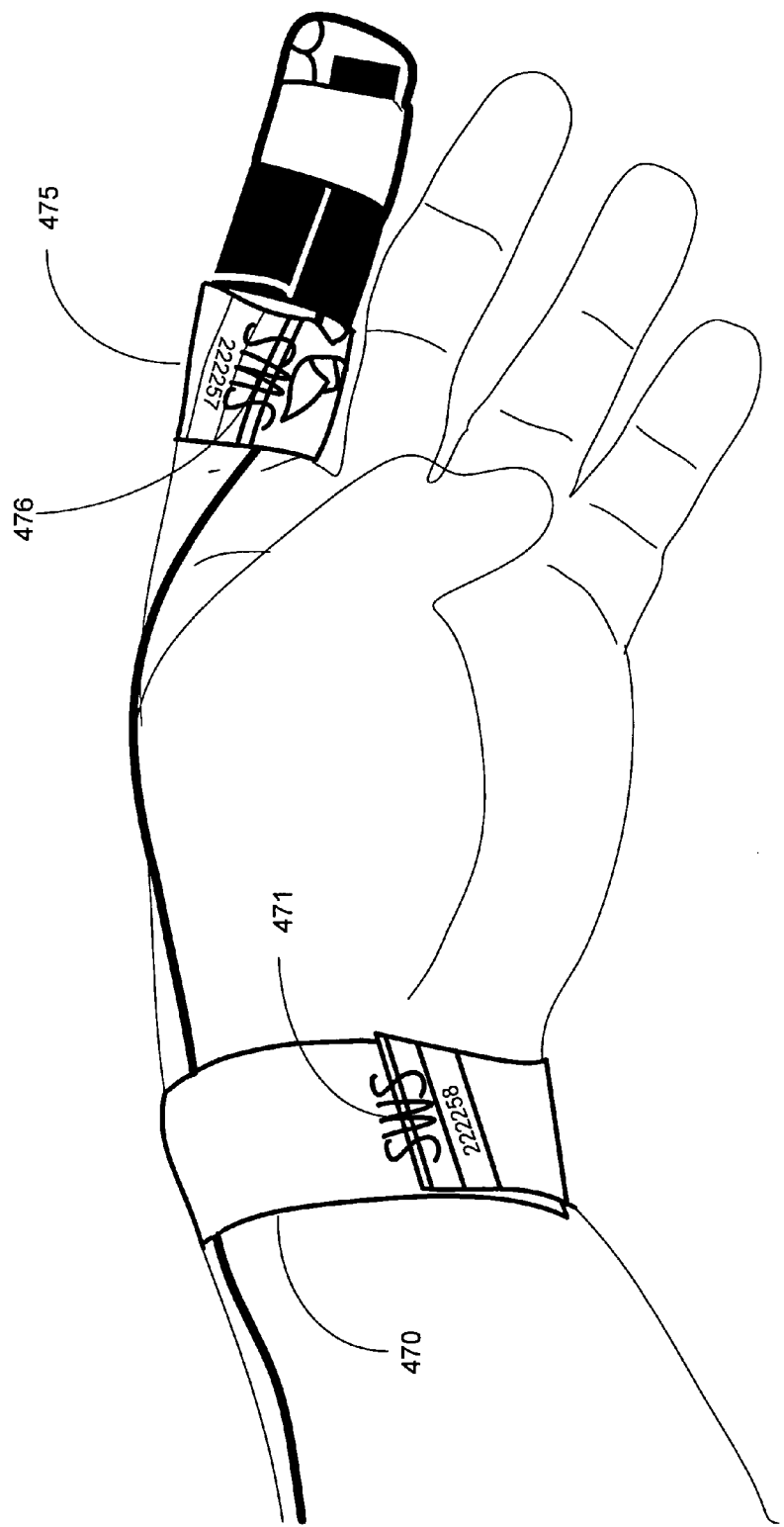
FIG. 4D illustrates a first and second identification band, each marked by the patient, in an arrangement to position a first and second serial numbers for viewing by a respiratory therapist.

FIG. 4D illustrates a first and second identification band, each marked by the patient, in an arrangement to position a first and second serial number for viewing by a respiratory therapist. In this embodiment, identification band 470 is marked at point 471 and identification band 475 is marked at point 476. For example the patient under test, such as a commercial truck driver, may mark each identification band with their signature or other mark for ensuring a "chain of custody" is established. The individual overseeing the test may mark the identification bands, either separate from or in combination with the patient's mark for improving test reliability.

Figure 4E:
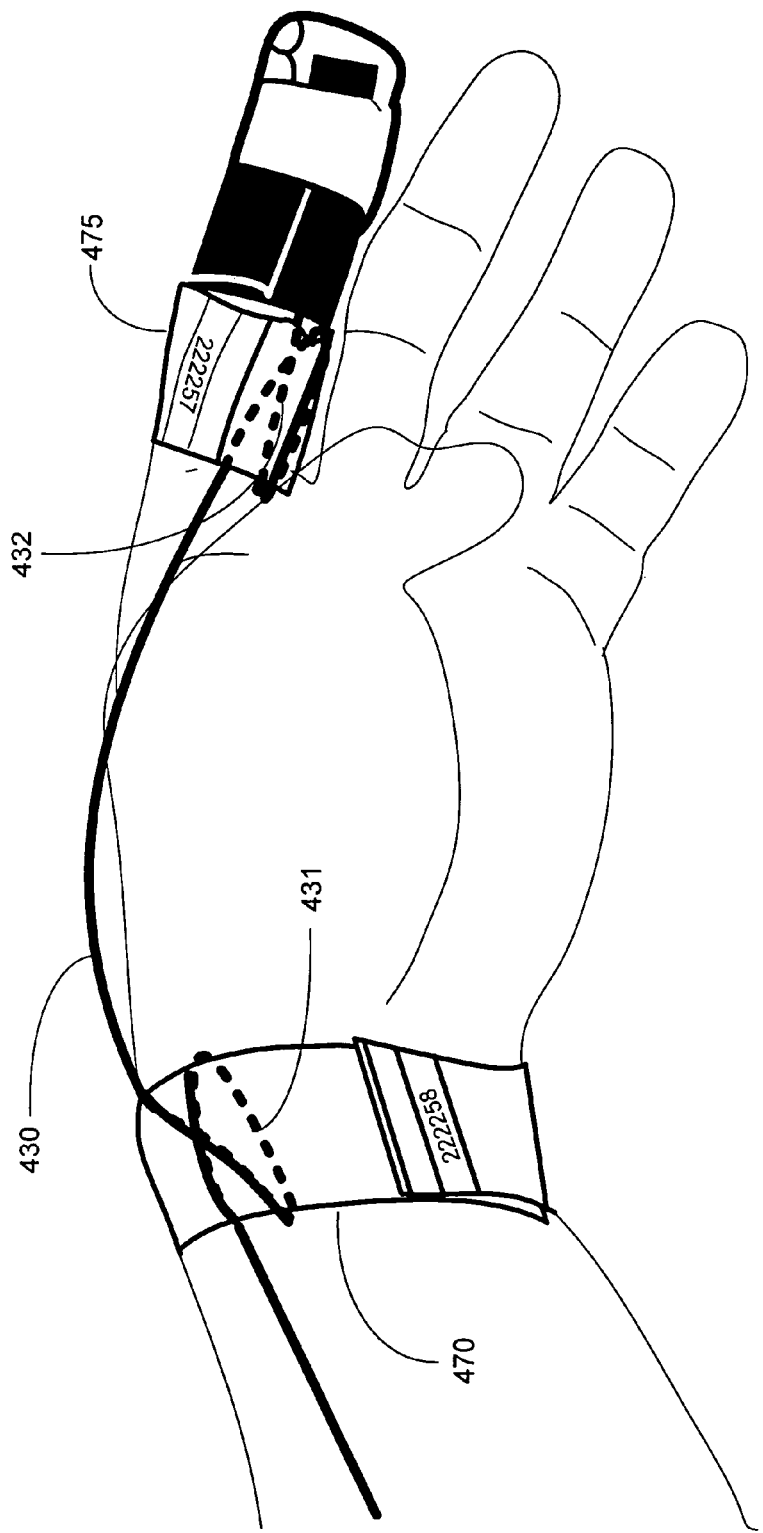
FIG. 4E is a perspective view illustrating a loop formed by a signal cable circling around a first identification band affixed at the index finger, and a loop formed by the signal cable circling around a second identification band affixed at the wrist.

FIG. 4E is a perspective view illustrating a loop formed by a signal cable circling around a first identification band affixed at the index finger, and a loop formed by the signal cable circling around a second identification band affixed at the wrist. FIG. 4E illustrates a further embodiment of the present design where the therapist may loop signal cable 430 around identification band 470 at point 431. In combination with or separately the therapist may loop signal cable 430 around identification band 475 at point 432, again for improving test reliability.

Figure 5A:
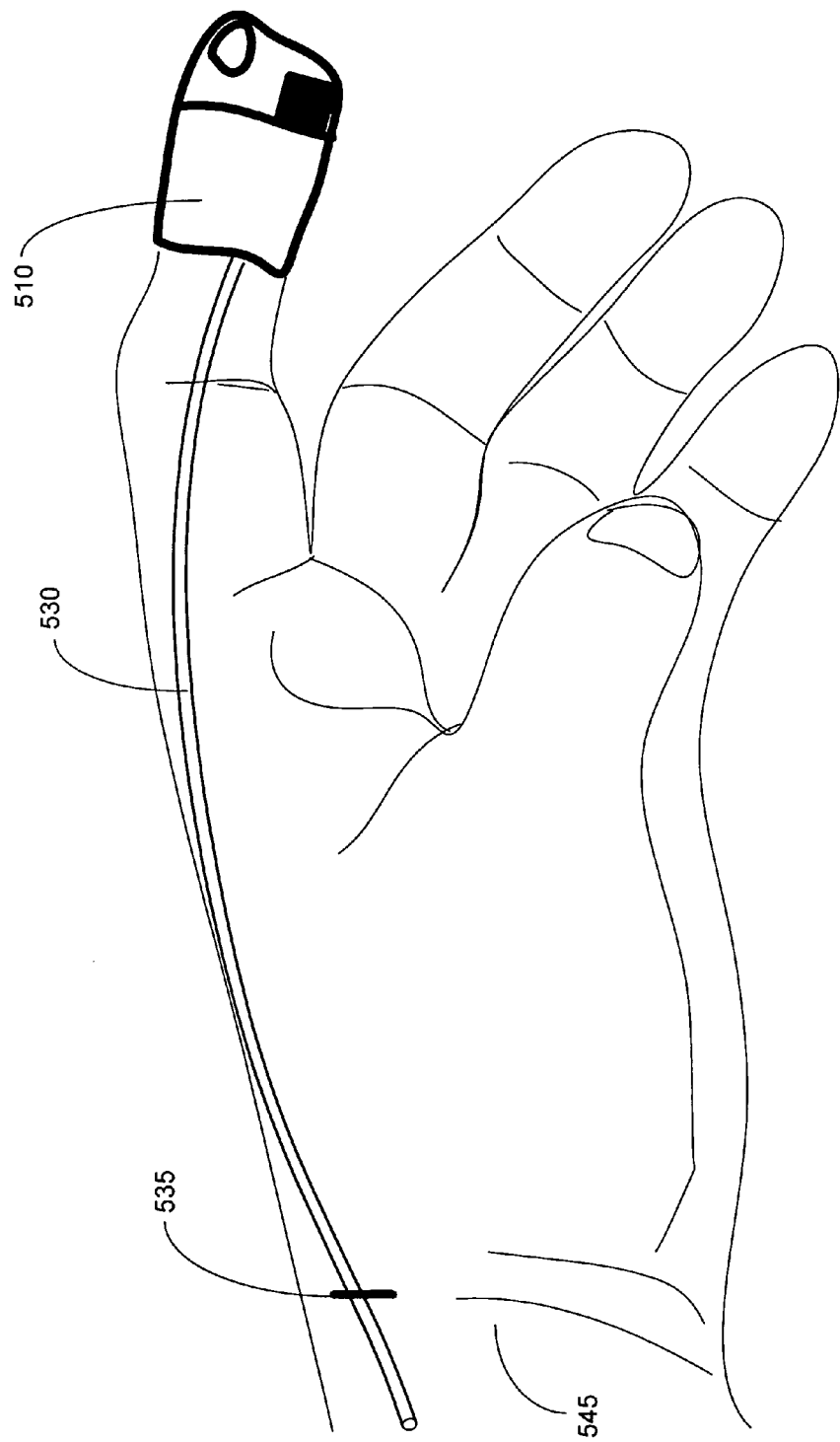
FIG. 5A represents a generalized view of an exemplary oxygen saturation sensing device design indicating where a respiratory therapist marks the signal cable at a crossing point formed when the cable meets a patient's wrist.

FIG. 5A illustrates a generalized view of an exemplary oxygen saturation sensing device design indicating where a respiratory therapist marks the signal cable at a crossing point formed when the cable meets a patient's wrist. In this embodiment the therapist may place mark 535 on cable 530 and patient wrist 545.

Figure 5B:
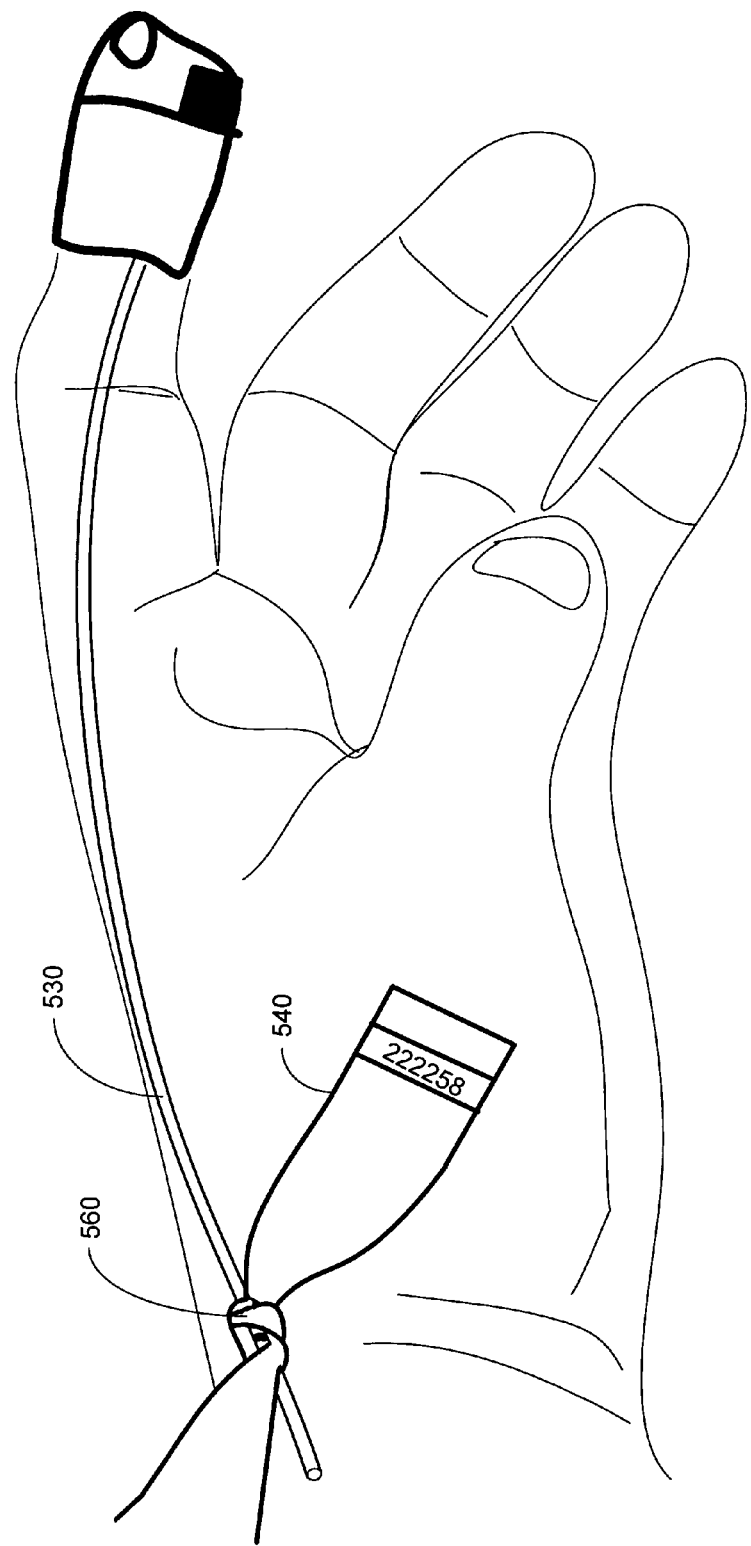
FIG. 5B shows a first identification band tied in a loose knot positioned at the mark on the signal cable.

FIG. 5B illustrates a first identification band tied in a loose knot positioned at the mark on the signal cable.

The respiratory therapist may configure identification band 540 by forming a loop arrangement available for routing signal cable 530 through the loop and then tighten the loop creating loose knot 560 in the identification band encircling around the signal cable.

Figure 5C:
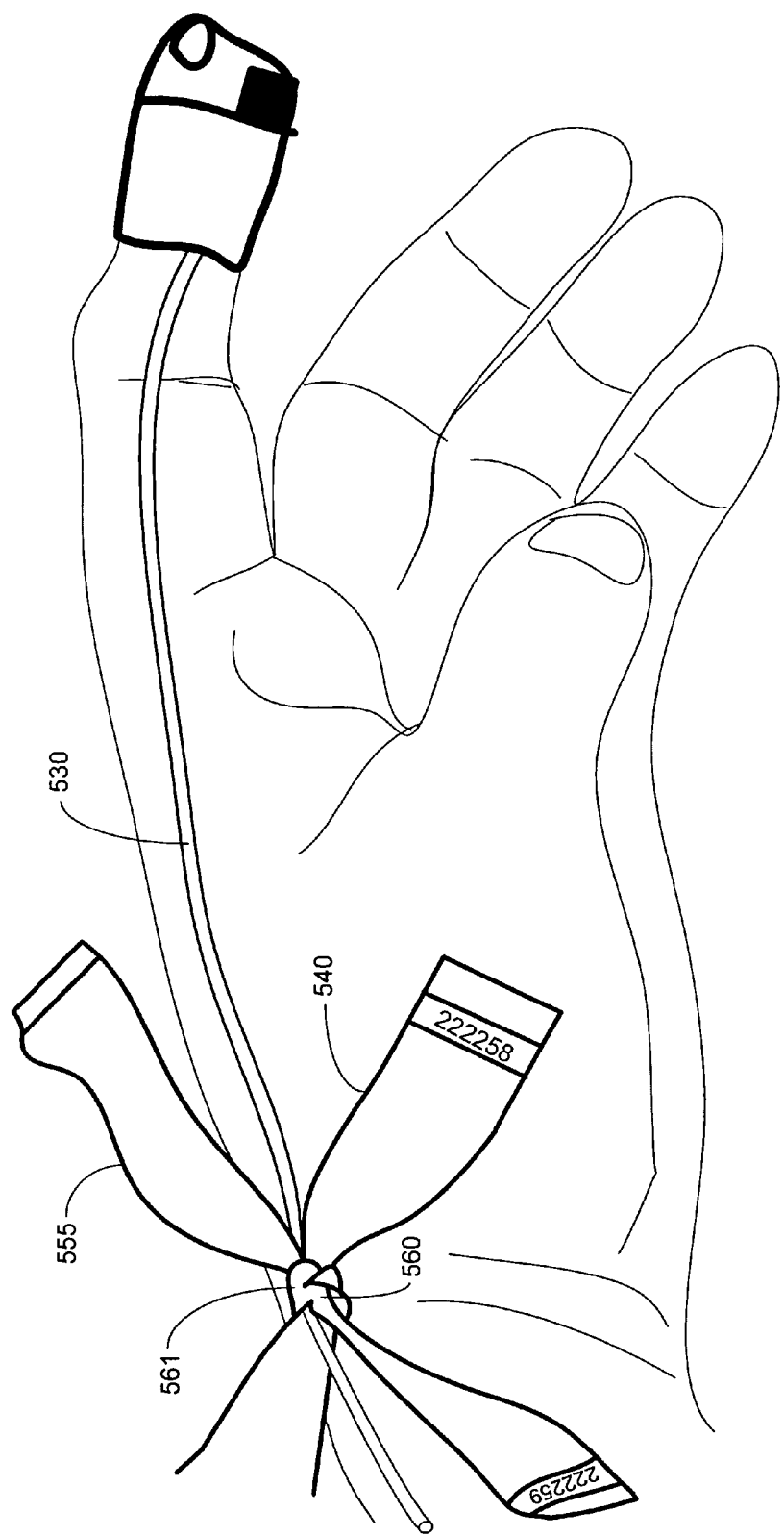
FIG. 5C illustrates a second identification band positioned through the loop formed by the first identification band and tied in a knot positioned at the mark on the signal cable.

FIG. 5C illustrates a second identification band positioned through the loop formed by the first identification band and tied in a knot positioned at the mark on the signal cable. The respiratory therapist may configure second identification band 555 by forming a loop arrangement available for routing signal cable 530 through the loop and then tighten the loop creating knot 561 in identification band 555 encircling around the signal cable. The therapist may ensure identification band 555 is pulled at each end to properly tighten knot 561 and identification band 540 is pulled at each end to properly tighten knot 560 are properly tied, tighten, and secured prior to placing in-use.

Figure 5D:
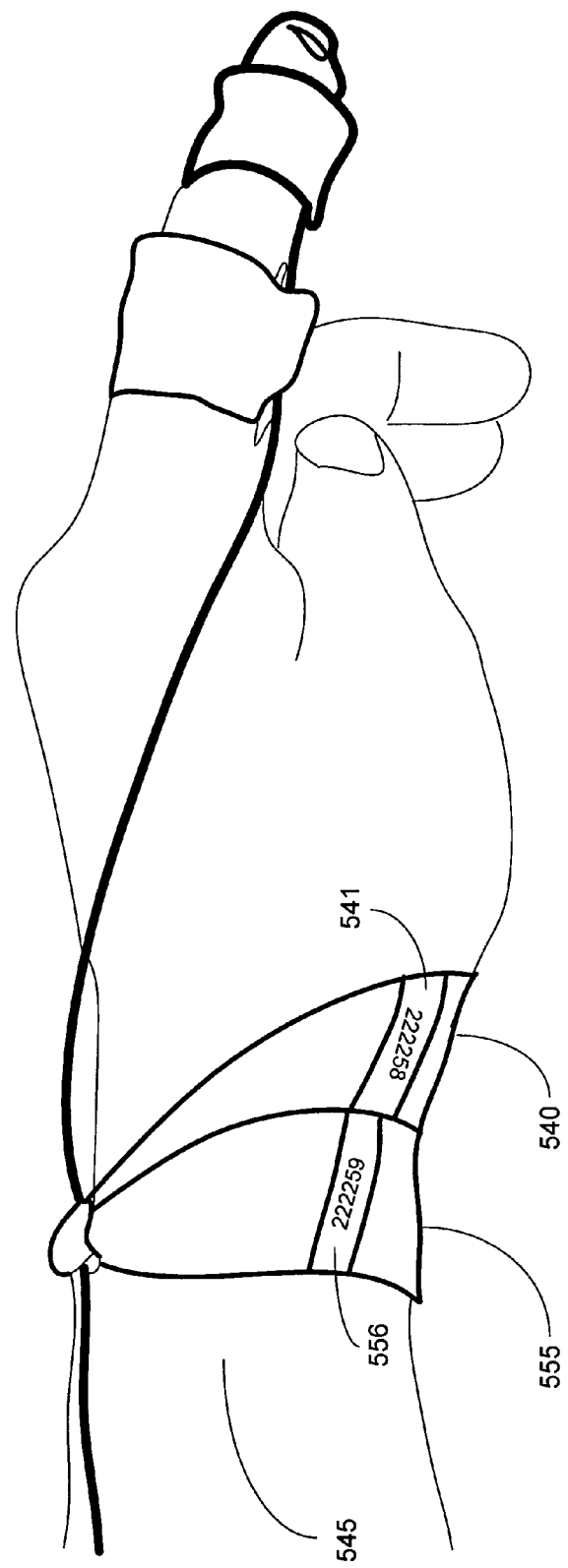
FIG. 5D is a first and a second identification band joined together at the mark on the signal cable and circling a patient's wrist.

FIG. 5D illustrates a first and a second identification band joined together at the mark on the signal cable and circling a patient's wrist. Identification band 540 may be affixed to itself and arranged to position serial number 541 for viewing by a respiratory therapist. After the knot is tightened around the signal cable, sufficient for securing the band to the cable, the respiratory therapist may wrap each end of identification band 540, in opposite directions, to encircle patient's wrist 545. In a similar manner, identification band 555 may be affixed to itself and arranged to position serial number 556 for easy viewing. The respiratory therapist may wrap each end of identification band 555, in opposite directions, to encircle patient's wrist 545. Each band may be affixed to the patient's wrist in according to instructions.

Figure 6A:
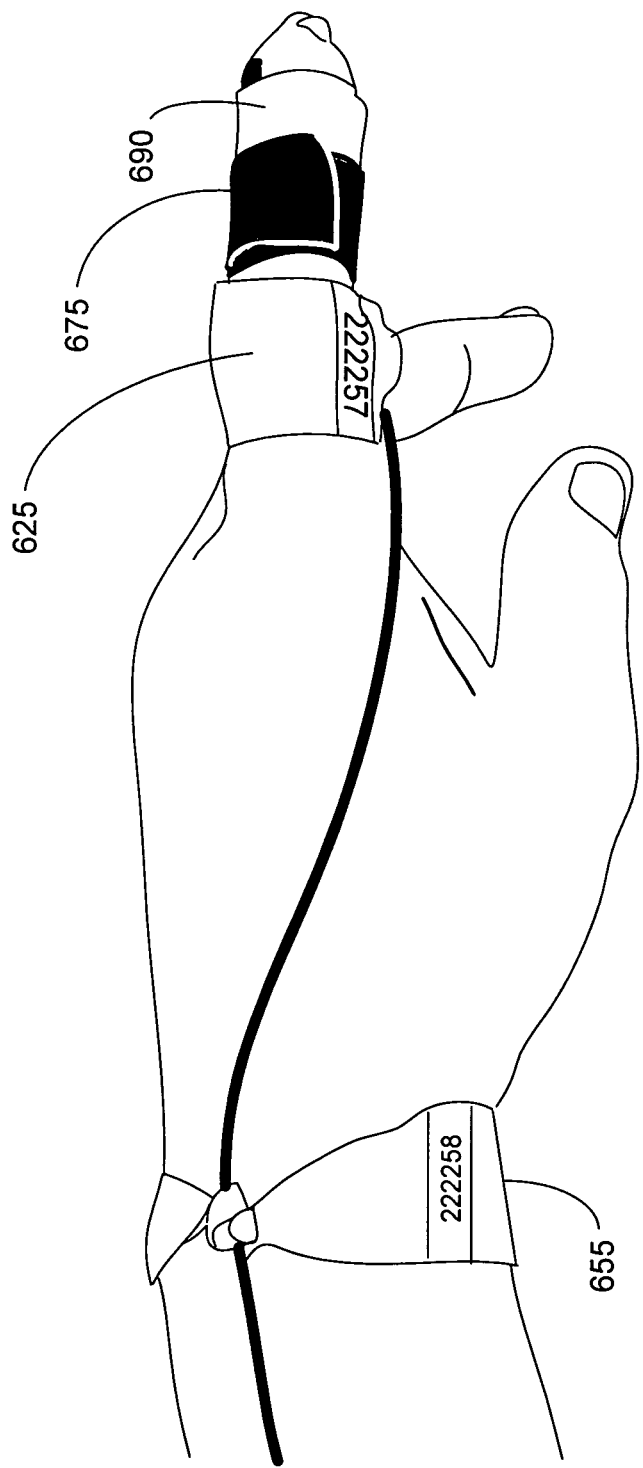
FIG. 6A shows the present design employing two identification bands in combination with a tape, positioned to cover an oxygen saturation sensing device and associated signal cable, wrapped to circle around a patient's index finger.

FIG. 6A illustrates the present design employing two identification bands in combination with a tape, positioned to cover an oxygen saturation sensing device and associated signal cable, wrapped to circle around a patient's index finger. A first identification band 625 may be affixed to the patient's index finger and a second identification band 655 may be affixed the patient's wrist as shown.

The identification bands are designed to shred and tear when removed. In this embodiment of the present design, the therapist may wrap tape 675 in a circle around a test individual's index finger positioned to cover pulse-oximetry sensor device 690 in combination with simultaneously covering the sensor's signal cable. Tape 675 is constructed from materials used to form the identification bands so that they exhibit shredding and tearing affects on removal.

Although shown using two bands, reliability and security may be realized when using a single band. In general, the present design may realized using at least one band, affixed at either the patient's index finger or wrist, and may include any combination and quantity of bands disclosed herein.

Figure 6B:
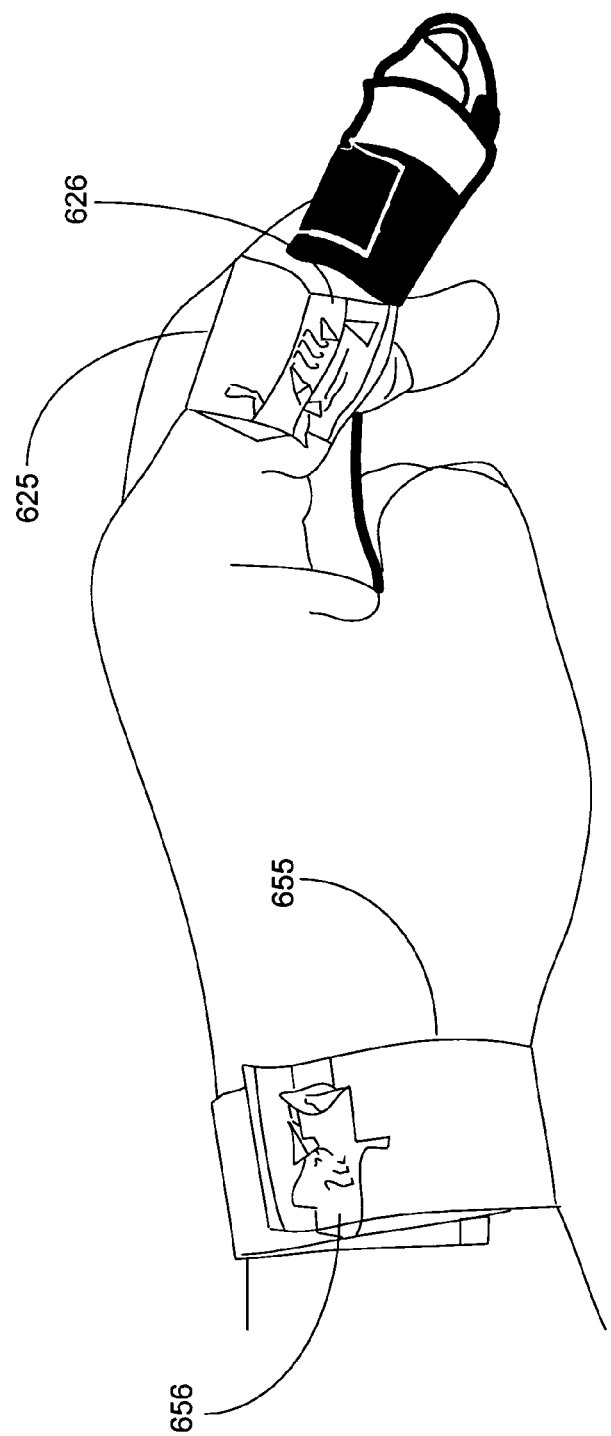
FIG. 6B illustrates a generalized view of two identification bands exhibiting tampering evidence.

FIG. 6B illustrates a generalized view of two identification bands exhibiting tampering evidence. First identification band 625 exhibits evidence 626 of fraud resulting from an attempt to remove the band. In addition, second identification band 655 exhibits evidence 656 resulting from an unauthorized attempt to remove the band.

Figure 6C:
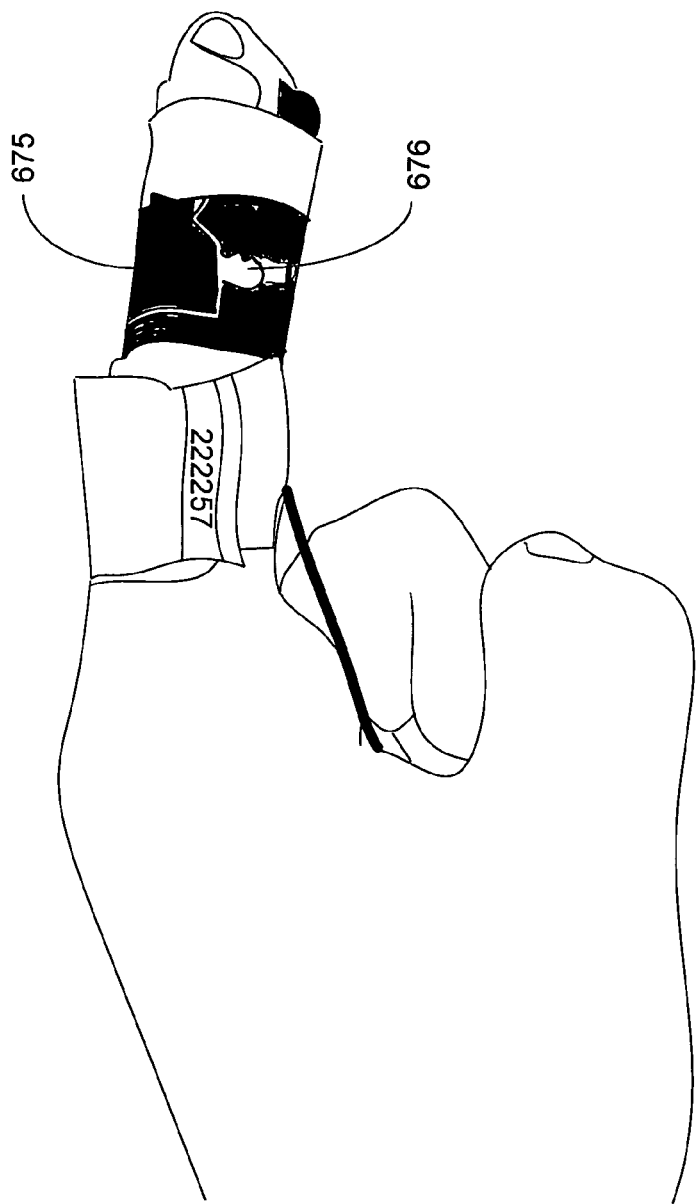
FIG. 6C represents a generalized view of a patient's index finger exhibiting a torn tape.

FIG. 6C illustrates a generalized view of a patient's index finger exhibiting a torn tape. Tape 675 exhibits evidence 676, in the form of shredding and tearing, resulting from an unauthorized attempt to remove the band.

In this arrangement, the present design may provide for an efficient and financially effective means for providing reliable oxygen saturation monitoring for ambulatory sleep apnea monitoring. The present design's protocol may provide for secure, tamper evident, uninterrupted measuring, for managing ambulatory testing.

Figure 7:
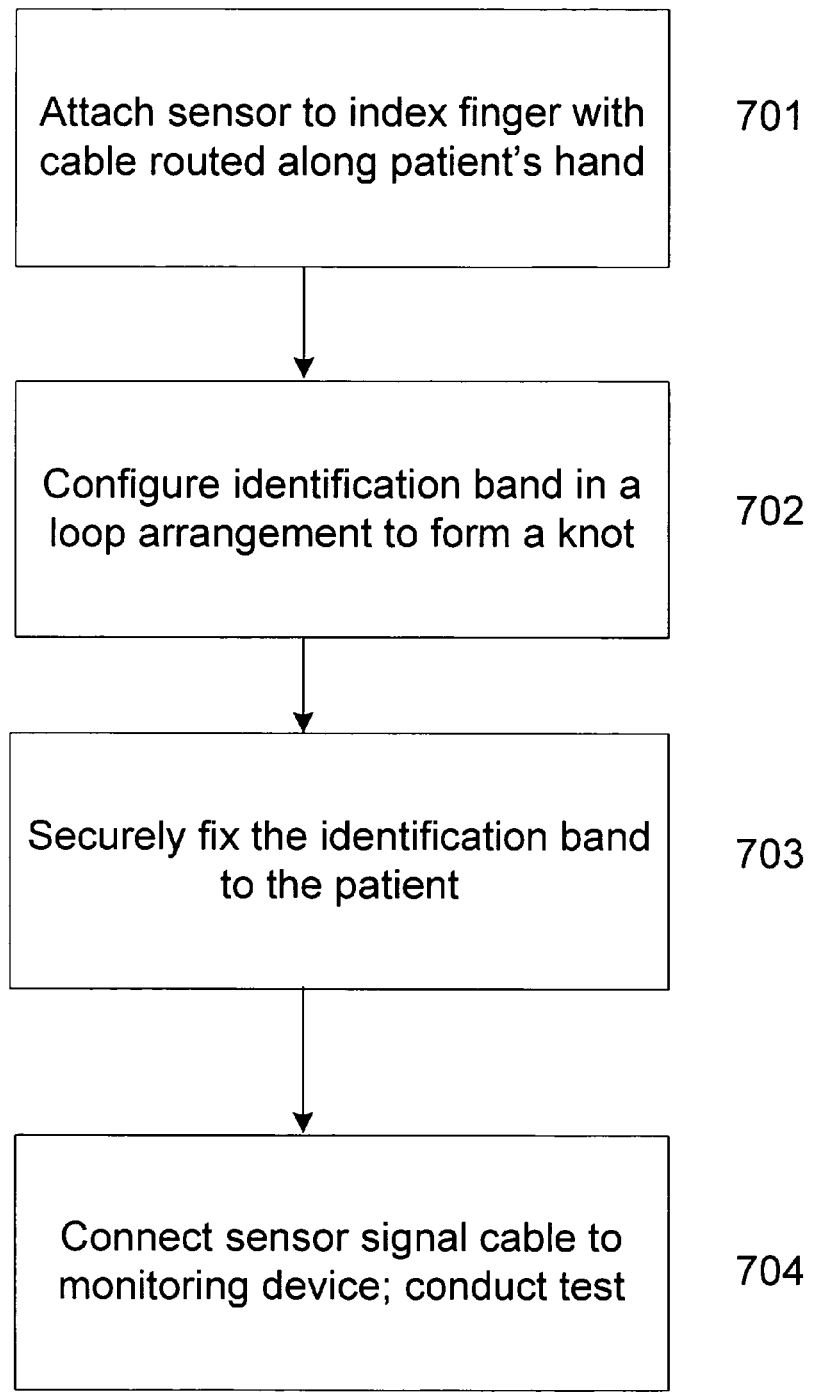
FIG. 7 is a flowchart showing operation according to one embodiment of the current design.

FIG. 7 illustrates the general protocol of the present design. From FIG. 7, box 701 indicates attaching a sensor, such as a pulse-oximetry sensor, to a test subject's index finger with a signal cable routed along the patient's hand. Box 702 represents configuring an identification band in a loop arrangement to form a knot where the signal cable is routed through the formed loop. Box 703 indicates securely fixing the identification band to the patient. Box 704 represents connecting a sensor signal cable, such as a pulse-oximetry sensor signal cable, to a monitoring device, such as a portable sleep diagnostic test or polysomnography monitoring system, during test conduct. The identification band is configured to encircle the patient's index finger and to shred and/or tear when removed.

Figure 8:
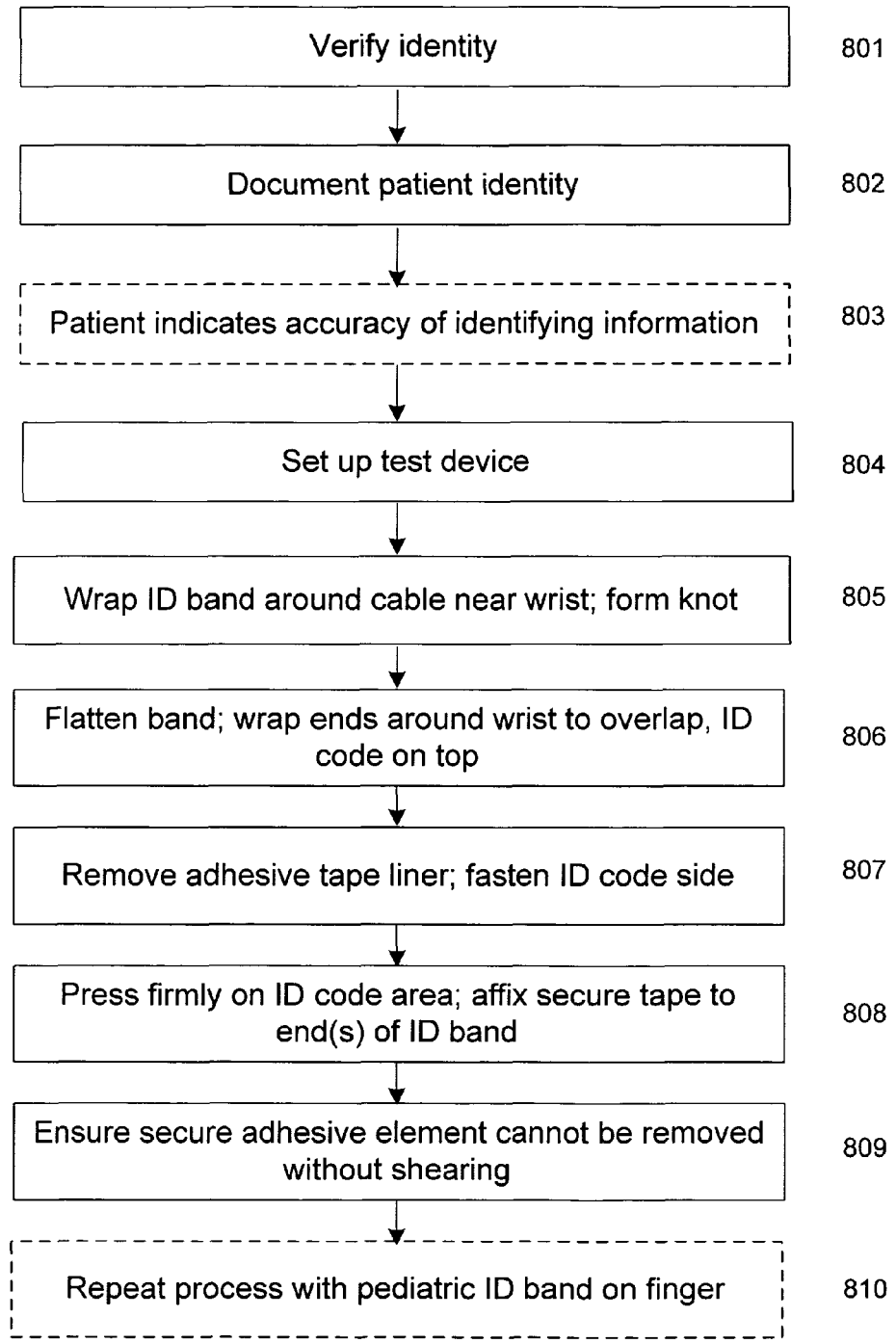
FIG. 8 illustrates a flowchart showing operation according to an alternate embodiment of the current design.

An alternative embodiment is shown in FIG. 8 and operates as follows. Initially, at box 801, appropriate personnel check the patient's identity, such as by using a driver's license to positively confirm identity. Box 802 represents documenting patient identity, such as on the test set-up form. Box 802 may also include documenting the ID band(s) being used, as well as serial number(s), (pediatric size and/or adult sized), and the date of the test. In optional box 803, the patient may indicate, such as via signature or otherwise, that the information is accurate. Box 804 represents setting up the test device. As described, this may entail placing the pulse-oximetry cable along the back side of the wrist of the non-dominant arm of the patient/test subject. Box 805 represents wrapping an ID band around the pulse-oximetry cable near the wrist area and tying a simple but tight knot in the band with the serial number facing away from the patient. Box 806 calls for flattening the band on both sides (with the serial code number side away from wrist), and wrapping the two ends around the wrist so they overlap with the unique ID code on top. Box 807 indicates removing the adhesive tape liner, and fastening that ID code side securely to the other end. Box 808 indicates that the operator/therapist presses down firmly on the ID code area to ensure it cannot be pulled back off without shearing. Box 809, which is optional, indicates repeating the process with pediatric ID band on finger with oximeter, in an area where patient would wear a ring. Subsequent to the foregoing, the test is performed.

The present design, certain embodiments involve the use of passive securing methods, such as an identification band forming a knot, loop or other arrangement around the sensor and associated cable. In further embodiments, the identification band may include an active component, such as employing wiring creating an electric circuit when the band is looped around the patient, and connected. The electric circuit design may be configured to monitor breaking of the electrical circuit to indicate tampering, such as monitoring voltage or current and recording when/if a reading goes to zero. Other forms of secure attachment to the patient may be employed.

Further, while several embodiments disclosed herein illustrate various loops used to attach the device to the patient, the present design is not limited in such attachment techniques. As described herein, multiple loops may be employed, as well as tapes, locking plastic arrangements or other materials that secure around the patient, Tyvek attachments, and so forth. And while the present device illustrates attachment around a wrist of a patient in several embodiments, other embodiments may attach to ankle/calf regions, neck, arm, around the head, or other appropriate locations on the patient depending on the needs of the test and requirements for securing. While sleep testing for apnea situations is disclosed, the present invention is not limited and may be used for other patient testing that may benefit from secure attachment to the patient.

In short, the present design may provide for tamper evident and tamper resistant ambulatory monitoring of a patient's oxygen saturation level, during the course of an overnight sleep study, and affords a high degree of control over the monitoring of signals generated from a pulse-oximetry sensor that advantageously positions and affixes the sensor and associated signal cable for reduced risk of fraud during test conduct. The system is thus configured to provide an identification band for fixing the signal cable to the patient's wrist or index finger. The identification band material is able to retain markings from a pen, stamp, or like writing instrument. In addition, a tape configured to shred and/or tear when removed may be wrapped around the sensor and cable in combination with using the identification band(s).

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A method for reliable oxygen saturation monitoring, comprising:
    attaching an oxygen saturation sensor to a patient at a first location on the patient;
    configuring a passive identification band in an arrangement connected to a sensor signal cable, wherein the oxygen saturation sensor is capable of being connected to the sensor signal cable, wherein the passive identification band does not employ wiring that creates an electric circuit within the passive identification band;
    securely fixing the passive identification band to the patient at a second location on the patient;
    connecting the sensor signal cable to a diagnostic test monitoring system;
    testing the patient; and
    marking the passive identification band,
    wherein the marking on the identification band is configured to evidence tampering when the passive identification band is removed.

2. The method of claim 1, wherein the passive identification band is configured to encircle the patient's wrist and to shred and/or tear when removed, further wherein the second location comprises the patient's wrist and the first location and the second location on the patient are not the same location.

3. The method of claim 1, wherein securely fixing the passive identification band further comprises placing a mark across the ends of the passive identification band.

4. The method of claim 1, wherein the passive identification band further comprises a unique serial number.

5. The method of claim 1, wherein configuring further comprises placing a loop in the sensor device signal cable, wherein the passive identification band is passed through the loop.

6. The method of claim 1, wherein the passive identification band is configured to encircle a connection formed where the sensor device signal output cable meets and connects with a PSG recording system input signal cable.

7. A method for monitoring a patient, comprising:
attaching an oxygen saturation sensor to a patient at a first location on the patient;
configuring a passive identification band in a secure arrangement at a second location on the patient, wherein the secure arrangement secures the sensor and a sensor signal cable to the patient, wherein the passive identification band does not employ wiring that creates an electric circuit within the passive identification band;
marking the passive identification band, and
connecting the sensor signal cable to a diagnostic test monitoring system for purposes of conducting a diagnostic test;
wherein the marking on the passive identification band is configured to evidence tampering when the identification band is removed.

8. The method of claim 7, wherein the passive identification band is configured to encircle the patient's wrist and to shred and/or tear when removed, further wherein the second location comprises the patient's wrist and the first location and the second location on the patient are not the same location.

9. The method of claim 7, further comprising a knot wherein the sensor signal cable is routed through a loop arrangement.

10. The method of claim 7, wherein the passive identification band comprises a unique serial number.

11. The method of claim 7, wherein configuring further comprises placing a loop in the sensor signal cable and the passive identification band is passed through the loop.

12. The method of claim 7, wherein the passive identification band is configured to encircle the connection formed where the sensor device signal output cable meets and connects with a PSG recording system input signal cable.

13. The method of claim 1, wherein the passive identification band encircles the second location of the patient's body.

14. The method of claim 1, further comprising a second band at a third location on the patient's body, the second band configured to evidence tampering when removed, wherein the first, second, and third locations on the patient's body are not the same location.

15. The method of claim 1, wherein the marking comprises a serial number, a pen marking, a signature, a marking relating to a chain of custody, a stamp, a writing instrument mark, a shredding of the band at a particular location, a tearing of the band at a particular location, a tear mark, or any combination thereof.

16. The method of claim 7, wherein the passive identification band encircles the second location of the patient's body.

17. The method of claim 7, further comprising a second band at a third location on the patient's body, the second band configured to evidence tampering when removed, wherein the first, second, and third locations on the patient's body are not the same location.

18. The method of claim 7, wherein the marking comprises a serial number, a pen marking, a signature, a marking relating to a chain of custody, a stamp, a writing instrument mark, a shredding of the band at a particular location, a tearing of the band at a particular location, a tear mark, or any combination thereof.

\* \* \* \* \*